United States Patent [19]

Manring

[11] 4,015,129

[45] Mar. 29, 1977

[54] POSITION INDICATING CONTROL METHOD AND APPARATUS IN RADIATION SCANNING SYSTEMS

[75] Inventor: John Michael Manring, Cleveland Heights, Ohio

[73] Assignee: Picker Corporation, Cleveland, Ohio

[22] Filed: Nov. 28, 1975

[21] Appl. No.: 635,949

[52] U.S. Cl. .............................. 250/360; 250/445 T
[51] Int. Cl.$^2$ ........................................ G01N 23/08
[58] Field of Search ............... 250/362, 363, 445 T, 250/360

[56] References Cited

UNITED STATES PATENTS

| | | | |
|---|---|---|---|
| 3,924,131 | 12/1975 | Hounsfield | 250/360 |
| 3,965,357 | 6/1976 | Hounsfield | 250/360 |

Primary Examiner—Alfred E. Smith
Assistant Examiner—T. N. Grigsby
Attorney, Agent, or Firm—Watts, Hoffmann, Fisher & Heinke

[57] ABSTRACT

A system and method are disclosed for sensing and controlling the operation of a transaxial reconstruction tomographic apparatus having a movable radiation source for directing radiation through a subject and a radiation detector movable synchronously with the source in an orbital path about the subject to detect radiation emerging from the subject.

The system includes circuitry and apparatus including an optical incremental encoder for producing index signals indicating when the detector passes predetermined locations in its orbital path, a frequency multiplier is responsive to the encoder for producing other more frequent signals indicating by interpolation the relative location of the detector with respect to the locations delineated by the index signals. Processing circuitry produces signals defining the boundaries of segments of the orbital scanning path, according to a scan segment magnitude and orientation indicated by the computational apparatus. The computational apparatus cooperates with the imaging apparatus for producing the image by separately treating discrete portions of information produced by the detector as it traverses respective segments of its orbital scanning path as indicated by occurrence by the frequency multiplied signals.

The frequency multiplication ratio between the frequency multiplied signals and the index signals is maintained constant by phase lock, loop feedback circuitry. The loop includes circuitry to control grossly the frequency of the frequency multiplied signals as a function of the speed of the detector (indicated by index signal frequency) while a phase comparator makes relatively small adjustments to maintain a constant frequency multiplication ratio between the index and frequency multiplied signals.

50 Claims, 7 Drawing Figures

POSITION INDICATING CONTROL METHOD AND APPARATUS IN RADIATION SCANNING SYSTEMS

References to Related and Relevant Patent Applications

U.S. patent application Ser. No. 559,411, filed Mar. 18, 1975, entitled TOMOGRAPHY SYSTEM HAVING NON-CONCURRENT COMPOUND AXIAL SCANNING (the SINGLE MOTION patent application);

U.S. patent application Ser. No. 559,412, filed Mar. 18, 1975, entitled TOMOGRAPHY SYSTEM HAVING AXIAL SCANNING the (DUAL MOTION patent application);

U.S. patent application Ser. No. 635,952 filed Nov. 28, 1975, entitled TRANSVERSE TOMOGRAPHY SYSTEM HAVING MULTIBEAM ORBITAL SCANNING WITH ALL BEAMS OFFSET FROM THE CENTER OF ORBIT (the BACKSIDE SCANNING patent application);

U.S. patent application Ser. No. 636,212 filed Nov. 28, 1975, entitled METHOD AND APPARATUS FOR IMPROVED RADIATION DETECTION IN RADIATION SCANNING SYSTEMS the (DETECTION patent application).

BACKGROUND OF THE INVENTION

1. Field of the Invention

This invention relates generally to systems for non-destructively examining objects using penetrative radiation and, more particularly, relates to an improved method and apparatus for measuring the intensity of X-radiation emerging from the subject of a clinical examination.

2. Description of the Prior Art

A conventional radiograph is a two-dimentional shadow image of a three-dimensional subject. The depth dimension is not apparent since all interior structures of the subject appear to be in a single plane. As a consequence in some circumstances, a conventional radiograph may fail necessary detail concerning relative spatial locations of interior structures, is difficult to interpret, and may not reveal the existence of a condition of interest in the subject.

Tomographic procedures have been developed to fulfill some objectives which are unobtainable by conventional radiographical procedures. In tomography, an image of the subject's internal structure, located in substantially only a single cross-sectional plane of interest extending through a subject, is produced by sequentially directing X-rays through the subject from a plurality of directions. The resulting image reveals relative spatial relationships of internal structures of the subject in substantially only the plane of interest.

Early tomographic systems utilized a radiation detector whose movement was coordinated with movement of a radiation source which directed a radiation beam to the detector. The source-detector pair simultaneously moved about an axis passing through the subject, and the system produced a cross-sectional image of the subject substantially in a plane of interest containing the axis about which the source-detector pair moved. The detector-source motion of this scanning technique resulted in substantially greater changes in the spatial relationship between the radiation beam and the subject's internal structure outside the plane of interest than between the beam and the structure within that plane. These greater changes blurred images of the structures out of the plane of interest and had little or no effect on images of structure in the plane of interest. In this manner our image of the structures in substantially only the plane of interest was produced.

Other tomographic procedures have been proposed which develop a cross-sectional image of the subject taken in a plane which includes the axis of the X-ray beam. Tomography which produces such images is known as transaxial tomography. This type of tomography produces an image, or representation, of a transverse section through the subject being examined, by generating a plurality of discrete portions of information, each portion representing a part of such an image, and "reconstructing" the image from the represented parts.

Reconstruction tomography scanning has evolved into two general types of systems. In one such system radiation is emitted as the source-detector pair are translated linearly with the beam axes in the plane of interest of the subject to be examined. A number of such translations or scans are completed during each examination of a plane of interest, with the orientation of the of linear translation being changed from one scan to another. Each scan, or single linear translation, is divided into individual scan segments. The radiation passing through the subject during each scan segment constitutes, in effect, a single beam passing through the subject along a narrow path in the plane of interest. The integral detected intensity of the beam passing through the subject during each scan segment is recorded for computing X-ray transmission (or X-ray absorption) characteristics of the patient. These characteristics are appropriately processed to provide a reconstructed image of the internal structure of the subject in the plane of interest.

In another type of transaxial reconstruction tomographic scanning system, a radiation source-detector pair orbits about the subject in a circular path with the axis of a beam in a plane of interest. After each orbit the source-detector pair is incrementally pivoted about an axis passing through the source and normal to the plane of interest. Another orbit is completed with the source-detector pair traveling along the same circular path, but at different relative orientation. Each orbital scan is formed by a continuous succession of individual scan segments. The integral intensity of the beam passing through the subject during each scan segment is detected and recorded for computing the X-ray transmission or absorption characteristics of the subject. The data accumulated from the scan segments is processed by computational processing circuitry to produce a reconstructed image in the plane of interest. Such computational apparatus can also be used to operate the scanner in accordance with a predetermined operational sequence.

In a modification of the "orbital" system, multiple detectors, closely spaced about the circular path, have been used with a common X-ray source. Use of multiple detectors enables, in some circumstances, production of good image resolution after only a single orbit scan of the source and detectors about the subject, rather than requiring several orbits. In effect, the single detector multiple scan approach is traded off, at least in some circumstances, for a multiple detector, single scan approach. This latter approach is described in the DUAL MOTION, the SINGLE MOTION, and the BACKSIDE SCANNING applications, referenced above.

Reconstruction transaxial tomography systems of both described types have commonly utilized a computational technique known as "back projection" for processing the collected radiation intensity data, image. The detected intensity of the X-ray beam passing through the subject along a given narrow path (defined by a single scan segment) is "back projected", or attributed, to all points in a reconstruction matrix which corresponds to the path of the beam. The values of radiation transmission intensity measured for all such paths during all the scans are back projected in the matrix to produce a segment-by-segment and scan-by-scan information buildup, or reconstruction, of the image.

More specifically, each value of the radiation transmission as it is back projected in the matrix for a given path is kept constant, and the respective values of each back projection at points of intersection of the respective paths are combined. Each point on the reconstructed image is therefore representative of the sum of the back projected intensities of the paths passing through the point. This technique is described in Kuhl, "A Clinical Radioisotope Scanner for Cylindrical and Section Scanning," PROC. SYMP., Athens 1964, Medical Radioisotope Scanning, I.A.E.A., Vienna, 1, 273, 1964, hereby expressly incorporated by reference.

The back projection technique has been improved with the introduction of filtered back projections and data processing using Fourier analysis. A discussion of Fourier reconstruction using filtered back projections is set forth in Chesler, "Positron Tomography and Three Dimensional Technique," PROC. SYMP. on Radio-nuclei Tomography, New York, N.Y., 1974. An algorithm for processing the data using convolutions on a digital computer is given in Shepp, et al, "Some Insights into the Fourier Reconstruction of a Head Section," Bell Laboratories, Murray Hill, N.J., 1974. Both the publications referred to in this paragraph are hereby expressly incorporated by reference.

In the orbital type of reconstruction tomography, the intensity of the detected radiation has been measured by integrating the data received from the detectors over the discrete time intervals during which the detectors traverse the respective scan segments, to produce signals each representing the average detected intensity over a segment. Early proposals for doing this employed a conventional integrator for integrating the data signal through the integration interval and an analog-to-digital converter for converting the integrated data signal to a digital value. This digital value, when compared with the duration of the integration interval, corresponding to the magnitude of the scan segment, represented the average detected intensity of the beam over the associated segment.

The method of processing the signals from the radiation detector in the described orbital system above requires integration over selected scan segments which often vary from one operating sequence to another of rotation of the orbital movement. In an operating sequence requiring repeated orbital scans, the scan segments of one scan are respectively rotationally offset by a small distance from the corresponding scan segments of a previous orbital scan. The reasons for this requirement in the operating sequence are explained in detail in the specifications of the DUAL MOTION, SINGLE MOTION and BACKSIDE SCANNING patent applications, expressly incorporated here by reference.

It is necessary to provide apparatus to accurately delineate the scan segment boundaries, this delineating apparatus should indicate to the computational apparatus the traversal of each scan segment by the detector and source. Since changes are often required in the size orientation of path segments, apparatus indicating traversal of scan segments must be flexible enough, to accommodate such variations.

In a previous proposed reconstruction transaxial tomographic scanner of the orbital motion type it has been proposed to generate signals indicating the rotational orbital position of the source and detector by a digital shaft encoder. Such an encoder was to be connected to a rotatable shaft mechanically connected to rotate as a function of the orbital rotation of the source and detector. In response to the rotation of the shaft, the digital encoder was to generate electrical signals indicating, within a given tolerance value, the rotational position of the source-detector combination.

While this proposed might have been satisfactory for some applications of tomographic scanners, the exacting requirements of precision, and flexibility of operating sequences of such scanners, have evoked a desire for greater accuracy (lower error tolerance) in the means for indicating scan segment traversal by the source-detector. The minute size of scan segments often used in operation of these scanners, (which minute size enhances system resolution) the fraction of degree offset orientation between scan segments of different scan orbits, and the variability of these sizes and offsets, has heightened the need for improved accuracy and resolution in providing indications of scan segment traversal.

Moreover, scanning orbit speeds vary by ratios as great as sixteen to one, (depending on the operational sequence selected) and the motion indicating control system must be capable of maintaining accuracy and stability throughout the full range of useful scan speeds.

SUMMARY OF THE INVENTION

A system embodying the apparatus and method of this invention includes a radiation apparatus having an information producing detector member movable along a predetermined path for sensing radiation from a subject and for producing information thereby describing a condition of the subject. Drive structure moves the movable member along the predetermined path. Other apparatus produces index signals indicating when the detector member passes predetermined points along the path. Computational and imaging apparatus and circuitry operates upon the information to derive an image describing the condition of the subject. Aspects of this invention include apparatus and circuitry for producing with improved resolution indications of the relative location of the movable member along its path intermediate the locations indicated by the index signals. Processing circuitry includes circuitry for providing, in response to the location indicating signals, signals indicating the boundaries of segments of the path traversed by the detector, according to scan segment magnitude and orientation called for by the computational apparatus. The computational apparatus separately responds to the information from the movable member developed during each scan segment to produce the image. Termination circuitry is provided to automatically stop the radiation apparatus in response to motion of the movable member past a predetermined point on its path, and steering circuitry prevents application of the location indicating signals to components during periods of their respective inoperability.

According to one aspect of the invention, the radiation system includes circuitry which multiplies the frequency of the index signals by a predetermined factor to indicate gradations in time and member movement between individual path locations delineated by the index signals, to enable the determination of the member position at intermediate points by interpolation. This feature provides adequate resolution in determining the location of the movable member along its path without necessitating the use of a digital shaft encoder, which is mechanically impracticable for indicating fine gradations of motion at speeds required in the application involved here.

Another aspect of this invention involves the application of a phase lock loop feedback circuit connected to the frequency multipher circuitry. The feedback loop includes a phase comparator having an output directed to the input of an amplifier, whose output is in turn connected to actuate the frequency multiplication circuitry. The feedback circuit assists in maintaining a constant frequency multiplication ratio between the index signals and the frequency multiplied signals, to insure accuracy in position representation by the multiplied signals.

One aspect of the feedback control circuit is the provision of a variable resistance component at the output of the phase comparator whose resistance is controlled by gain varying circuitary as a function of the frequency of the index signals. This gain varying circuitry causes the resistance of the variable resistance component to vary substantially inversely with the frequency of the index signals. This variation assists in maintaining substantially constant the gain of the feedback loop, notwithstanding frequency changes in the index signals, and hence enhances the stability of the feedback circuit.

Another feature of the feedback circuitry includes circuitry connected to the amplifier for varying the amplifier input as a function of the frequency of the index signals. This feature provides for a gross adjustment of the center frequency of the frequency multiplied signals, as a function of the index signal frequency. This feature thus provides the circuitry with flexibility to accommodate changes in the index signal frequency, while maintaining constant the factor of frequency multiplication. Small adjustments in the frequency of the multiplied signals obtained by operation of the phase comparator, to maintain a constant frequency multiplication ratio between the frequency multiplied location indicating signals and the index signals.

The processing circuitry, according to one aspect, includes circuitry for storing a signal representing a predetermined magnitude of path segment length, and for repeatedly providing an indication each time the movable member has traversed a path segment, the traversal being indicated in response to sensing of the frequency multiplied signals.

According to another feature of the invention, this circuitry adjusts the magnitude of the predetermined path segments, as dictated by the computational apparatus.

Still another aspect of the invention is the provision in the processing circuitry for determining (again, as dictated by the computational apparatus) the degree to which the path segments, whose boundaries are indicated by the processing circuitry, are offset with respect to a predetermined point on the path of movement. This feature facilitates operation of the apparatus in operations where repeated scanning motion of the member is required, and the path segments over which discrete quantities of information are utilized must vary somewhat from one scan to another.

Another feature of the invention is the provision of circuitry for automatically terminating operation of the apparatus when the movable member reaches another predetermined location in its path of motion.

A more specific feature of the processing circuitry of this invention includes steering circuitry to prevent application of the multiplied signals to circuit components during times in which the components are inoperative during the operating sequence. This feature avoids the possibility of generation of spurious signals in the processing circuitry.

These and other aspects of the invention will be understood from the following detailed description and drawings in which.

DESCRIPTION OF A PREFERRED EMBODIMENT

Figure 1:
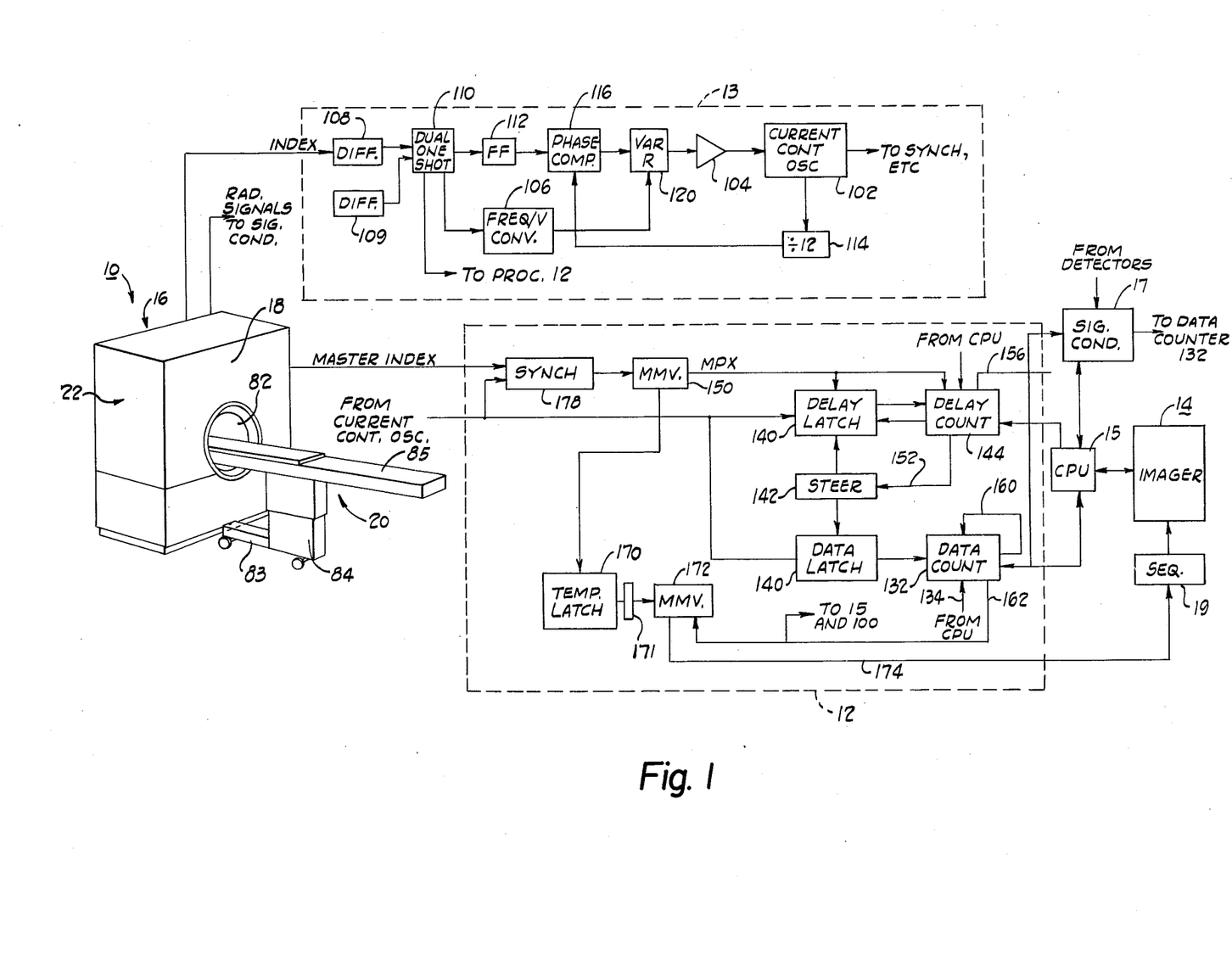
FIG. 1 is a partially perspective, partially schematic drawing of a radiation scanning system incorporating the present invention.

A transverse section X-ray tomography system embodying the present invention is illustrated schematically by FIG. 1. The tomography system includes an X-ray scanning unit 10 for scanning a subject with X-rays in a given plane and producing electrical output information in the form of signals descriptive of the radiation sensed in the scanning procedure; imaging apparatus 14 and computational apparatus 15 for producing an image of a portion of the subject from the radiation descriptive signals; a signal conditioning circuit 17 for interfacing the radiation signals with the computational apparatus; a position indicating system 13 for producing indications of motion of a component of the scanning unit 10 which indications are coordinated with the radiation signals to facilitate production of the image by the computational apparatus 15 and imager 14; a processing unit 12 for receiving and processing the position indicating and other signals and producing signals therefrom indicating traversal by the movable member of segments of its path as defined by the computational apparatus; and a sequencer 19 for controlling the operation of the scanning, computational and imaging units for tomographic system operation according to a predetermined operational sequence.

Except as otherwise provided here, the tomography system incorporating this inventive system and method is described in detail in the above referenced SINGLE MOTION, DUAL MOTION, DETECTION and BACKSIDE SCANNING patent applications.

The imager 14 can be a display device using a cathode ray tube or an image printing device, either of which can be operated from the computational apparatus output. Suitable imager devices are already known and therefore the imager 14 is not further illustrated or described in detail. This signal conditioning circuit 17 is described in detail in the reference DETECTION patent application.

A scanning system 10 constructed according to a preferred embodiment of the invention is illustrated schematically by FIGS. 1–4 and includes a supporting assembly 16, a scanning assembly 18 movably supported on the assembly 16, and a subject supporting table 20.

The supporting assembly 16 includes a main frame unit 22 (see FIGS. 2–4) which is positioned on a floor of a building in which the system 10 is located, a chassis-like housing assembly 24 (FIG. 1) supported by the main frame for enclosing the assemblies 16, 18, and a drive unit 26 (see FIG. 2) for moving the scanning assembly 18 relative to the supporting assembly 16.

Figure 2:
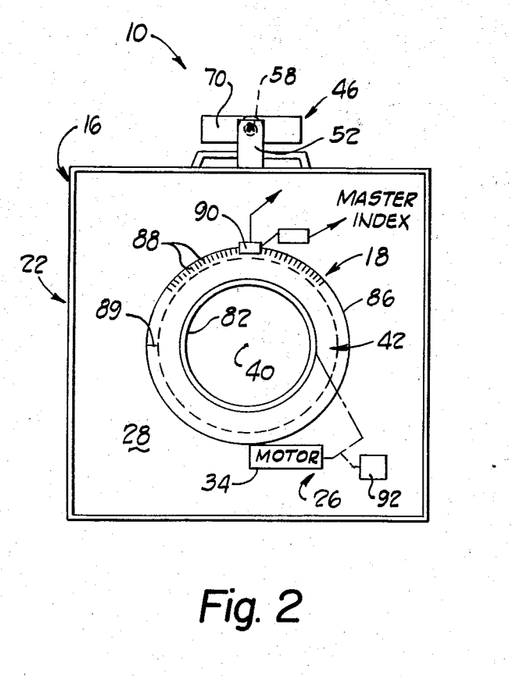
FIGS. 2–4 are views of a scanner used in the scanning system of FIG. 1.
Figure 3:
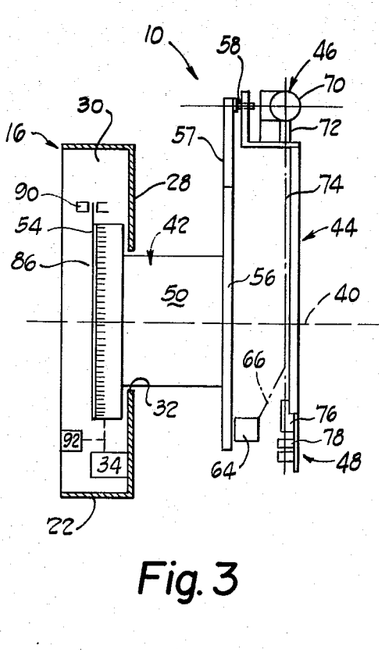
Figure 4:
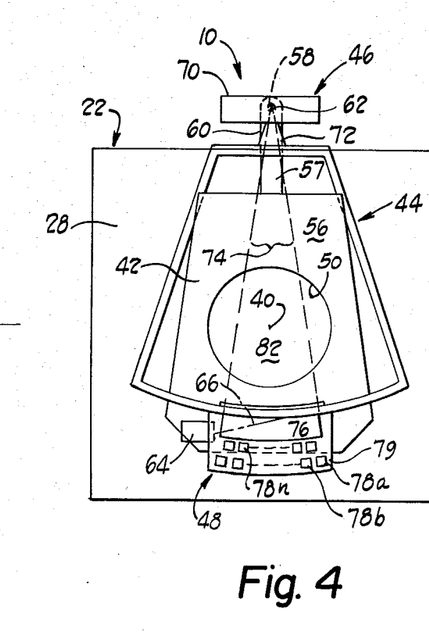

The frame unit 22 includes an upright plate-like rectangular body 28 having a peripheral stiffening flange portion 30 projecting from its circumference transverse to the plane of the body 28. A mounting aperture 32 for the scanning assembly 18 is defined centrally in the body plate 28 and the drive unit 26 is supported on the frame adjacent the aperture 32. The drive unit 26 preferably includes an electric motor 34 drivingly connected to the scanning assembly 18 via an associated drive transmission 36 (schematically illustrated) of suitable construction.

The scanning assembly 18 is connected to the frame 22 for rotation about an axis 40 extending through the aperture 32. The scanning assembly 18 includes a rotatable support unit 42 journaled to the frame 22, a framework 44 movably connected to the support unit 42, and X-ray source and detection assemblies 46, 48, respectively, which are mounted at spaced apart locations on the framework 44. The X-ray source and detection assemblies 46, 48 are rotatable with the support unit 42 and orbit about the axis 40 relative to the frame 22 and are adjustably movable, with the framework 44, relative to the support unit 42.

The support unit 42 includes a tubular cylindrical body 50 extending through the aperture 32 coaxially with the axis 40 and supported on the frame 22 by bearings (not shown) for rotation about the axis 40. A radially outwardly extending flange structure 54 is formed at the end of the body 50 adjacent the frame 22 and the projecting end of the body 50 carries a surrounding flange-like mounting plate 56. The mounting plate 56 includes a projecting arm 57 which carries a trunnion 58 to which the framework 44 is connected.

The framework 44 is preferably constructed from lengths of angle irons which are welded together at their ends to define a generally flat, open frame, and a bearing arm structure 60 extending from the frame to the trunnion 58 so that the framework, along with the supported source and detection assemblies, can pivot about the axis 62 of the trunnion relative to the supporting unit 42. The rotation axis 40 extends through the open center of the framework so that the framework about the axis 40 with the unit 42.

A positioning drive motor 64 supported by the plate 56 controls the position of the framework 44 relative to the supporting plate 56 via a suitable transmission schematically illustrated by the reference character 66. The motor and transmission are constructed and arranged so that when the framework is positioned as desired with respect to the axis 62 it is positively locked in the adjusted position.

The X-ray source assembly 46 is schematically illustrated and since it may be of any suitable or conventional construction is not described in detail. As illustrated the X-ray source assembly includes an X-ray tube head 70 defining an X-ray focal spot 71 on the pivot axis 62 and a collimator 72 associated with the tube head for directing X-radiation toward the detection assembly 48 in a fan-shaped beam configuration 74 which is preferably only about 2 millimeters deep.

The X-ray detection assembly 48 is supported by the framework 44 opposite the source assembly 46 and includes a collimator 76, a plurality of X-ray detector units 78a–78n, and a supporting apron 79 for the collimator and detector units.

The collimator 76 is supported in the path of the X-ray beam 74 and defines a series of narrow slots corresponding in number to the number of detector units 78 so that a narrow pencil beam of X-rays impinges on each detector unit 78. Any reasonable number of detector units can be employed, and twenty such units have been selected for use in one scanning unit.

The detector units may be of any suitable or conventional structure and each preferably includes an X-ray excitable scintillation crystal element which is optically coupled to a photomultiplier tube.

The source assembly 46 and the detection assemblies 48 are fixed with respect to each other on the framework 44 so that as the support unit 42 rotates, the source and detection assemblies orbit about the axis 40 while the beam 74 is continuously directed from the source to the detection assemblies 48.

The housing assembly 24 (see FIG. 1) is detachably connected to the frame 22 and extends about the scanning assembly 18 to protect and prevent unauthorized access to internal components of the scanning system.

The component parts of the scanning unit 10 are formed to define a central generally cylindrical opening 82 extending through the scanning unit coaxially with the rotation axis 40. The diameter of the opening 82 is sufficiently large to surround a human torso alinged with the axis 40.

The subject supporting table 20 is schematically illustrated (FIG. 1) as including a wheeled supporting base 83, a pedestal 84, and a subject supporting table top 85 projecting from the pedestal. A supine human subject on the table top 85 is advanced into the opening 82 until a desired section of the subject's body is disposed in the plane of the X-ray beam 74 and with the rotation axis 40 extending through the subject.

The support unit 42 is then rotated about the axis 40 with the X-ray source assembly 46 operated to scan the subject with the beam 74. Since the beam 74 is simultaneously directed to multiple X-ray detector units, a single orbit of the source and detection assemblies about the the subject effectively produces a number of scans corresponding to the number of detector units employed in the detection assembly 48. If (as is sometimes the case) the reconstructed image resolution provided by a single orbit of the source and detection assemblies about the subject is not sufficient, the framework 44 is pivoted relative to the unit 42 about the trunnion axis 62 and another orbit is completed. This procedure (described in the above referenced relevant patents and applications) is followed until a desired degree of image resolution can be produced.

During each orbit of the source and detection assemblies the scanning unit produces radiation, index, and master index signals which are respectively transmitted to the apropriate one of the processing unit 12 position indicating system 13 and signal conditioning circuit 17 to enable eventual construction of an image.

The radiation signals are analog electrical signals which are continuously produced by each X-ray detector unit and have values which vary in direct relationship to the intensity of the X-ray beam impinging on the respective detector unit. The radiation signals are individually output from the respective detector units 78a–78n to the signal conditioning and computational units 17, 15.

Each orbital scan of the source and detection assemblies is broken up into a succession of individual scan segments during which X-rays impinging on each detector have traversed a narrow path through the subject. In the preferred embodiment the index signals are constituted by a series of pulses, each of which indicates termination of one portion of scanning motion and the initiation of the next succeeding portion. The index signals are produced by an incremental encoder illustrated in FIGS. 2 and 3 as including an annular timing disc 86 attached to the body flange 54 and bearing a series of substantially equally spaced marks 88 about its periphery and a photosensitive signal producing element 90, such as a photodiode, mounted on the frame 22 adjacent the periphery of the timing disc 86. The markings 88 are accurately located with respect to the timing disc and each other and are preferably spaced at 1/10 degree intervals around the axis 40. Whenever one of the marks 88 moves to a predetermined location relative to the element 90, the element 90 produces a pulse forming an index signal of the pulse train.

Preferably, the incremental encoder also includes structure for producing a master index signal each time the timing disc passes a predetermined point in its rotational motion. This structure includes a single another mark or indentation 89 at the predetermined point on the disc, and a second photosensitive apparatus 91, similar to the photosensitive unit 90, for producing a master index pulse signal each time the mark 89 passes a predetermined point in the rotation of the wheel.

The angular velocity of the support unit 42 is maintained substantially constant throughout the period of a complete orbital scan of the subject and accordingly the index signal pulses are of generally uniform frequency. The index signals thus provide, in effect timing signals which, when modified in a manner described below, define the end and beginning of successive individual scan segments.

Preferably, the drive structure 26 provides for adjustability in scanning speeds from 30 revolutions per minute (r.p.m.) down to 1⅞ r.p.m. depending on the nature of the operating sequence selected for the scan. Within individual orbits, however, the scanning speed is maintained constant.

FIG. 1 shows in block form the position-indicating system 13 and processing unit 12. The position-indicating system 13 generates position indicating frequency multiplied signals showing the rotative position of the rotatable source and detectors of the scanning unit 10. The position indicating signals are directed to the processing unit 12 and the signal conditioning circuitry 17 to enable the use of the radiation signals from the scanning unit 10 by the computational apparatus 15 to operate the imager 14 to produce a desired image of the subject.

The processing unit 12 includes circuitry illustrated in block form within the dotted box designated 12 in FIG. 1, and generates data interval signals which indicate divisions between scan segments. The computational apparatus and signal conditioning circuitry 15, 17 responds to the radiation signals from the scanning unit 10 and to the data interval signals to cause the imager 14 to produce the desired image of the subject in the plane of interest. The computational apparatus 15 produces signals to the processing unit 12 indicating the selected magnitude of each scan segment for a particular operational sequence selected, and also indicates the rotational orientation of the scanning segments with respect to a predetermined point in the orbital path of the source and detectors represented by the occurrence of the master index signals. The computational apparatus 15 responds to the radiation signals and the data interval signals from the processing unit 12 to cause the imager 14 to reconstruct an image of the subject based on discrete quantities of information borne by the radiation signals occurring during each individual scan segment of motion by the detectors.

The position-indicating system 13 responds to the index signal occurring at each 1/10th degree of rotation of the scanning unit source and detectors 70, 78a–h, to produce 12 equally spaced frequency multiplied pulses for each occurrence of an index pulse. Moreover, these signals, multiplied by a factor of 12, are maintained in synchronism with the index pulses, in order that the uniformly-spaced multiplied signals accurately represent gradations of motion of the rotatable components of the scanning unit 10 between each index signal occurrence. Thus, the position-indicating system 13 emits a train of pulses carrying information indicating gradations of the rotational position of the rotatable components of the scanning unit 10 to within 1/120th degrees.

The multiplied signals from the position-indicating system 13 are generated by a frequency multiplier embodied by a current controlled oscillator 102. The current controlled oscillator 102 produces a pulse train output, the frequency of which is proportional to the magnitude of a DC current applied as an input thereto. The current input to the current controlled oscillator 102 is furnished by an operational error amplifier 104, which responds to a voltage input thereto to produce an output current which is proportional to the voltage input. The voltage input is produced by a frequency-to-voltage converter 106, which responds to a pulse train input of a given frequency to produce a DC output voltage whose magnitude is a direct function of the frequency of the input. The index signals drive the frequency-to-voltage converter 106 and are transmitted by a differentiator 108, a monostable multivibrator (one-shot) 110, and a flip-flop 112. The differentiator 108 is connected to receive the index signals from the scanning unit 10 and process them in known fashion to make them more readily discernible to the multivibrator one-shot 110. The flip-flop 112 performs a "divide by 2" function, and presents substantially a square wave to the frequency-to-voltage converter 106, having a frequency equal to half the frequency of the index signal pulse train.

In operation, the parameters of the frequency-to-voltage converter 106, the amplifier 104, and the current controlled oscillator 102 are adjusted in known fashion to provide for an overall frequency multiplication of 24 for the multiplied signal, with respect to the frequency of the signal produced by the flip-flop 112.

Thus, such adjustment of these parameters establishes the center frequency of the multiplied signals produced by the oscillator 102 subject only to undesirable minor variations caused by circuit drift, noise, and the like.

A phase lock loop feedback control circuit, including a scaler 114 and a phase comparator 116, is employed to maintain a precise frequency relationship between the signals produced by the flip-flop 112 and the frequency multiplied signals produced by the current-controlled oscillator 102. Such maintenance of frequency relationship substantially nullifies the undesirable effects of circuit drift, etc., referred to above, which would otherwise cause the frequency multiplication factor of the current-controlled oscillator 102 to be somewhat non-uniform. The scaler 114 performs a "divide by 24" function on the multiplied signals from the oscillator 102 to nominally accord these signals a frequency the same as that generated by the flip-flop 112. The phase comparator 116 receives the signals from the flip-flop 112 and from the scaler 114, and produces a DC voltage output which is a function of the phase difference between these two signals. When these signals are in quadrature the phase comparator 116 produces no output, and has no effect on the circuit. When, however, the signals are not in quadrature, the phase comparator 116 produces a relatively small DC error voltage which is also input to the amplifier 104 and which thereby operates on the current-controlled oscillator 102 to bring the multiplied signals generated by that oscillator back into synchronous lock with the signals from the flip-flop 112.

Preferably, the parameters of the phase comparator 116 are adjusted such that its effect on the current controlled oscillator 102 is relatively minor with respect to that of the frequency-to-voltage converter 106. In the preferred embodiment, the phase comparator 116 is adjusted to have a maximum effort on the output frequency of the controlled oscillator 102 of approximately plus or minus 20% of that produced by the frequency-to-voltage converter 106.

The position-indicating system 13 is also provided with gain control circuitry including a variable resistance component 120 for maintaining relatively constant the gain of the feedback loop described above, regardless of variations in index signal frequency. The maintenance of uniform gain enhances the stability of the circuitry and also favorably adjusts time constants of circuitry associated with the error amplifier 104 to minimize unwanted transients and possible resultant instability and inaccuracy. The variable resistance component 120 is controlled by the frequency-to-voltage converter 106 to interpose in the output of the phase comparator 116 a resistance which is substantially inversely proportional to the frequency of the index signals produced by the scanning unit 10.

The processing circuitry 12 includes circuitry responsive to the computing apparatus 15 to establish the magnitude and orientation of the scan segments for the particular selected operational sequence. The processing unit 12 transmits data interval signals to the reconstruction circuitry 100 and computational apparatus 15, each data interval signal defining the end of each scan segment and the beginning of the next. The data interval signals are generated by a data counter circuit 132. The data counter circuit 132 produces the data interval signals in response to the input thereto of a number of the multiplied signals from the position indicating system 13, corresponding to a motion increment of the rotatable detector and source members of the scanning unit 10 over a scan segment whose magnitude is determined by a signal input to the data counter 132 over a lead 134 from the computational apparatus 15. The frequency multiplied signals are gated to the data counter 132 by way of a data latch circuit 140.

The condition of the data latch 140 is dictated by steering circuitry 142. The steering circuitry 142 normally conditions the data latch 140 to pass the multiplied signals from the position indicating system 13 to apply them to the data counter 132. The condition of the steering circuitry 142 responds in turn to a delay counter circuit 144, a delay latch circuit 146, and a monostable multivibrator one-shot 150.

The delay counter circuit 144 stores a delay magnitude signal from the computing apparatus 15 representing a nominal selected degree of offset of the scan segment boundaries from the rotational position of the rotatable scanner and source members of the scanning unit 10 denoted by the occurrence of the master index signal generated by the photosensitive apparatus 91. The delay counter 144 responds to the multiplied signal train from the system 13 which is gated through the delay latch circuit 146 to produce a delay interval signal upon a lead 152 when the number of frequency multiplied signals applied to the delay counter 144 represents a delay motion increment having a magnitude equal to that represented by the delay magnitude signal from the computational apparatus 15.

The delay latch circuit 146 is responsive to the occurrence of the master index signal, transmitted by the one-shot 150, to initiate the gating of the frequency multiplied signals through the delay latch 146 to the delay counter 144. The delay counter 144 is responsive to the master index signal to load the delay magnitude signal from the computational apparatus 15 into storage circuitry of the latch, so that the delay counting operation can begin.

Previous to the cumulative application of the number of frequency multiplied signals equivalent to the motion increment represented by the delay magnitude signal, the delay counter 144 produces a signal on the lead 152 which causes the steering circuitry 142 to prevent the application of frequency multiplied signals to the data counter 132 by so conditioning the data latch 140. Subsequent to the application of sufficient frequency multiplied signals to represent the delay interval magnitude indicated by the delay interval signal, the delay counter actuates the steering circuitry 142 to initiate the application of frequency multiplied pulses to the data counter 132 by way of the data latch 140.

In many operating sequences for the tomographic scanning system, there is no offset of the scanning segment desired and consequently the delay interval signal represents zero delay. Under these circumstances, the delay counter responds immediately upon actuation by the master index signal to cause the steering circuitry 142 to open the delay latch gate and permit frequency multiplied signals to flow to the data counter 132.

The steering circuitry 142, in response to the condition of the delay counter 144, actuates both the delay latch 146 and the data latch 140 to perform their gating functions. One aspect of this operation is that the delay latch circuit is conditioned to substantially prevent the application of frequency multiplied signals to other components, i.e., the delay and data counters 144, 132, when such components are in an inoperative state in the operating sequence. Specifically, when the delay counter actuates the steering circuitry 142 to inhibit the passage of frequency multiplied signals to the data counter 132, the delay latch 146 is conditioned to allow the passage of frequency multiplied signals to the delay counter 144. Conversely, when the steering circuitry 142 is conditioned to pass frequency-multiplied signals through the data latch circuitry 140 to the data counter 132, the application of such signals to the delay counter 144 is prevented by suitable conditioning of the delay latch circuit 146 by the steering circuitry.

Under circumstances in which the selected operational sequence dictates the existence of a delay offset of the scan segments, the operation is as follows: the master index signal simultaneously loads the delay magnitude signal into the delay counter 144 and initiates the passage of frequency-multiplied signals through the delay latch 146 to the delay counter. Also, the steering circuitry 142 prevents frequency-multiplied signals from being applied to the data counter 132. This condition continues until the rotatable source-detector members of the scanning unit 10 have rotated (as indicated by the number of frequency-multiplied signals supplied to the delay counter) through a delay interval motion increment equivalent to that represented by the delay interval magnitude signal from the computational apparatus 15. At that time, the delay counter 144 produces a delay interval pulse on a lead 156 which is directed to the computational apparatus 15 to indicate the beginning of the first scan segment so that the computational apparatus 15 may begin to process the information carried by the radiation signals during the scan segment. Upon the production of the delay interval signal, the steering circuitry is actuated to apply the frequency-multiplied signal to the data counter 132. The data counter 132 produces a data interval signal indicating the end of the scanning segment, when, as noted above, sufficient frequency-multiplied signals are applied thereto to represent motion equivalent to the scan segment magnitude indicated by the signal on the lead 134. In response to this condition, the data counter 132 produces a data interval signal on two leads 160, 162. The data interval pulse on the lead 160 serves to reset the data counter to reload the signal appearing on the lead 134, representing segment magnitude. This reloading operation, and the continued application of the frequency multiplied signals to the data counter 132, results in repeated operation of the data counter 132 to generate data interval signals marking the beginning and end of successive scan segments, the magnitude of each of which is indicated by the signal on the lead 134, which is repeatedly restored in the data counter 132 after execution of each scan segment. The data interval signal appearing on the lead 162 is applied to the signal conditioning circuitry 17 and the computational apparatus 15 to indicate the end of each successive scan segment, similarly to the fashion in which the delay interval signal indicates the beginning of the first of such segments.

The processing unit 12 also includes termination circuitry for stopping the operation of the tomographic apparatus when the rotatable source-detector members of the scanning unit 10 have rotated through a predetermined arc. In this preferred embodiment, the termination circuitry ceases the operation of the tomographic apparatus when the movable detector members have moved through substantially an entire revolution, the completion of which motion is defined by the occurrence of a second master index signal. The circuitry for accomplishing this feature includes a temporary memory latch 170, a gate 171 and a monostable multivibrator one-shot 172. The temporary memory latch 170 responds to the occurrence of a second master index signal to enable the gate 171 and the monostable multivibrator 172 to produce a termination signal in response to the occurrence of the next occurring data interval signal following the occurrence of the second master index signal. The data interval signal is input to the one-shot 172 through the enabled gate 171 over the lead 162. Once conditioned by the temporary memory latch 170, and gate 171 the one-shot 172 produces a termination signal over a lead 174 directed to the computational apparatus 15, in response to which the computational apparatus causes the tomographic apparatus to terminate its operation.

A synchronizing circuit 178 is interposed between the scanning unit 10 and the multivibrator 150, to synchronize more precisely the master index signal with a substantially simultaneously occurring frequency multiplied signal, so that the multivibrator 150 produces substantially simultaneously, a frequency multiplied signal and a master index signal.

Figure 5:
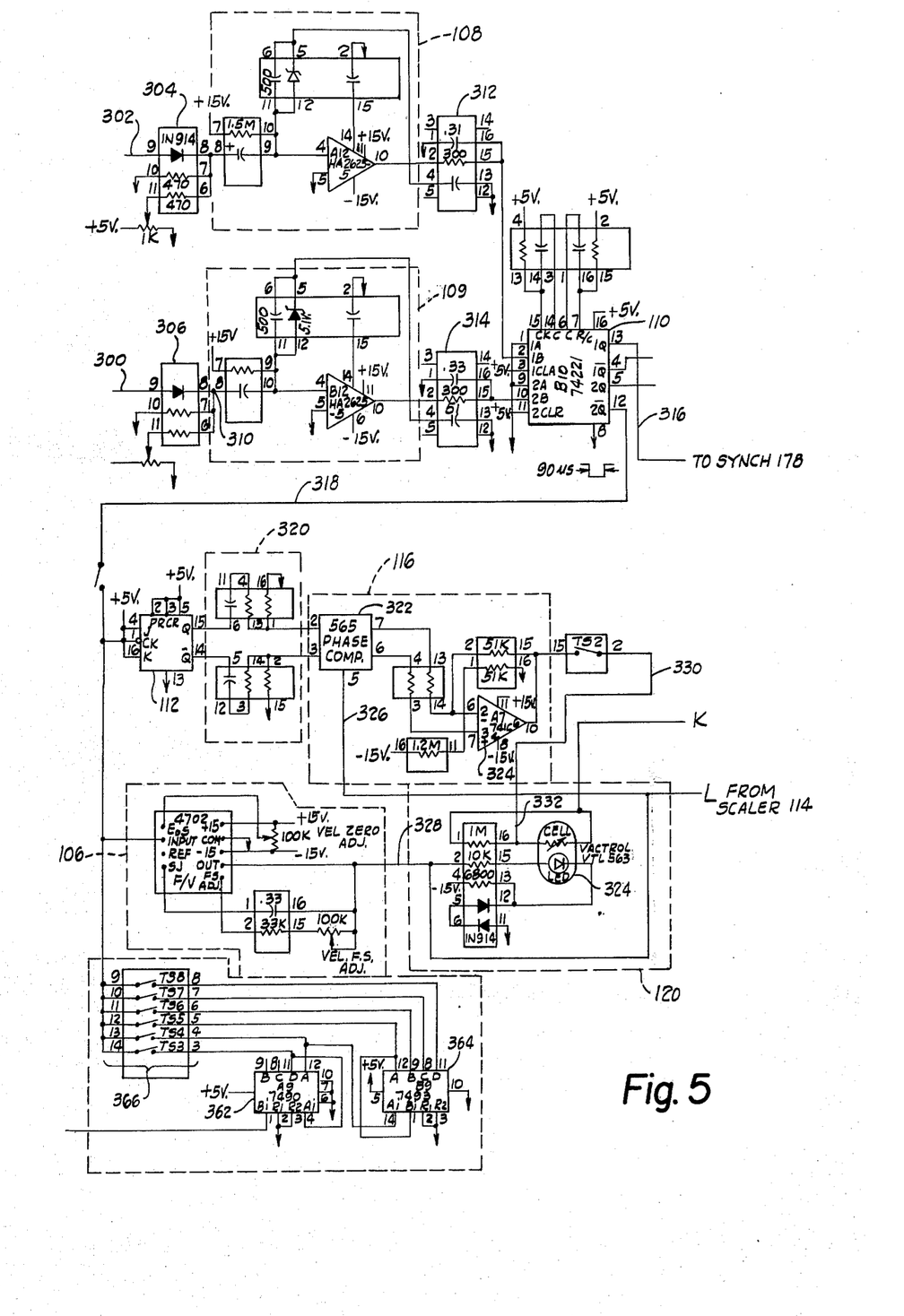
FIGS. 5–7 are circuit schematics of portions of the scanning system illustrated in FIG. 1.
Figure 6:
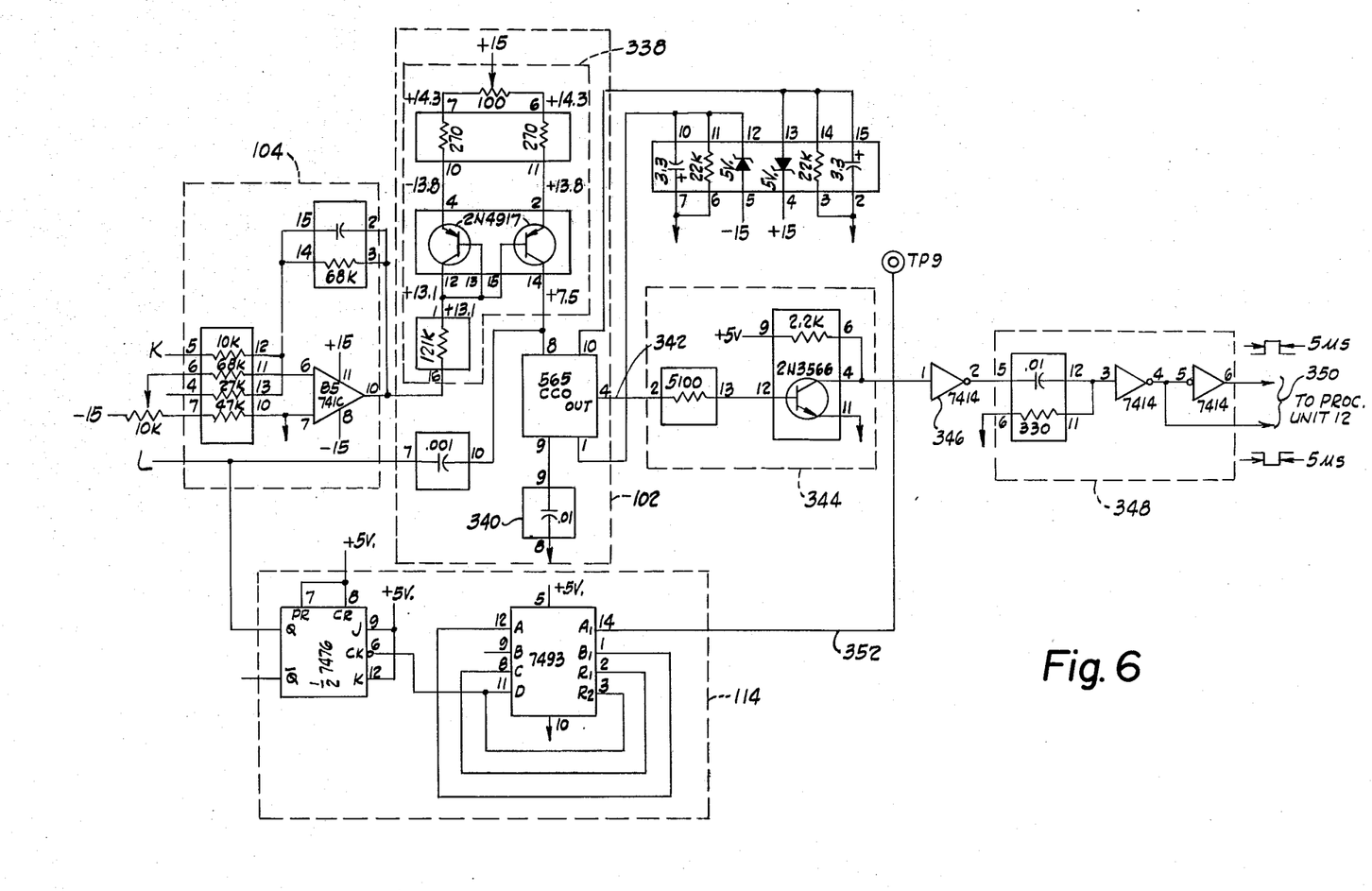

FIGS. 5 and 6 illustrate schematically the position indicating system 13 of this invention. Insofar as the components of the position indicating system 13 are constituted by integrated circuit components, the numerical designation and pin number connections of each of these integrated circuit components are illustrated in FIGS. 5 and 6.

Referring to FIG. 5, the index signals from the scanning unit 10 are applied on a lead 300, while the master index signals are applied on a lead 302. The leads 300, 302 feed a pair of threshold devices 304, 306, respectively. The threshold devices 304, 306 are beneficial because the photosensitive devices producing the index and master index signals from the scanning unit 10 produce output signals which are rather "hump" shaped, and which are more easily differentiated (as explained below) if the upper portions of the wave forms are isolated. Accordingly, the threshold devices produce outputs on two leads 308, 310, respectively, which outputs represent only the upper portion of the index and master index signal wave forms, respectively.

The outputs on leads 308, 310 feed the pair of differentiators 108, 109, respectively. The outputs of the differentiators 108, 109 are respectively passed through a pair of low pass filters 312, 314 to eliminate noise, from which they are directed to the dual one shot monostable multivibrator 110. The dual one shot 110 directs pulses corresponding to the master index signals over a lead 316 to the synchronizing circuit 178, for processing in a manner discussed in detail below. Another output of the dual one shot 110, corresponding to the index signals, is directed over a lead 318 to the flip-flop 112 and to an input of frequency-to-voltage converter 106.

The output from the flip-flop 112 is directed through an attenuator 320 having an attenuation ratio of approximatey 8:1, from which the output is directed to the phase comparator 116. The phase comparator 116 includes an integrated circuit element 322 and a level translator including an amplifier 324 and its associated circuitry as illustrated. The phase comparator 116 also receives as an input from the scaler 114 a signal on a lead 326. The phase comparator 116 operates to produce on a lead 330 a voltage signal whose average value is proportional to the phase differential between the signals from the attenuator 320 and from the scaler 114.

This output from the phase comparator 116 is directed over a lead 332 as an input to the variable resistance circuitry 120. The variable resistance circuitry 120 includes a variable resistance photosensitive component 324 whose resistance is a function of the magnitude of an input signal appearing on a lead 328 and generated as an output of the frequency-to-voltage converter 106. The frequency-to-voltage converter 106 produces on the lead 328 a DC voltage signal which is proportional to the frequency of the index signals appearing on the lead 318 and directed to the frequency-to-voltage converter.

The output from the phase comparator 116 is attenuated by the variable resistance component 120 as a decreasing function of the output from the frequency-to-voltage converter 106, and appears upon a lead designated K which is directed to an input of the error amplifier 104 (see FIG. 6).

Among the functions of the variable resistance component 120 is that of facilitating the maintenance of substantially constant loop gain in the phase lock feedback loop. This assists in maintaining the stability of the feedback loop, notwithstanding changes in the frequency of the index signals input to the system resulting from changes in the rotating speed of the scanning unit 10. Also facilitating stability is the fact that the resistance changes brought about by the operation of the frequency-to-voltage converter and the variable resistance component 120 favorably affect time constants of the circuitry associated with the error amplifier 104, maintaining substantially constant magnitudes of transient phenomena and the like. Preferably, the variable resistance component is designed to vary its resistance substantially inversely with respect to the index signal frequency.

The output from the error amplifier 104 is passed through a voltage-to-current converter 338 to the current controlled oscillator 102. The parameters of the output of the current controlled oscillator 102 are controlled by the value of a timing capacitor 340.

The output of the current controlled oscillator appears on a lead 342, and represents the frequency multiplied signals which are utilized in the processing unit 12 for controlling the tomographic system. These frequency multiplied signals are passed through a level translator 344 whose function it is to translate the level of the frequency multiplied signals to facilitate their processing by the logic circuitry of the processing unit 12, discussed in detail below.

The output of the level translator 344 is directed through an amplifier 346 and a one shot designated as 348. The output from the one shot 348 appears on a pair of leads 350, (each of which is the inverse of the other, and frequency multiplied signals are directed to the processing unit 12).

Feedback from the current controlled oscillator 102 and its associated level translator 344 is directed back to the phase comparator 116 by way of a lead 352, which passes through the scaler circuitry 114 whose function it is to divide the frequency of the output from the level translator 344 by a factor of 24. The output from the scaler circuitry 114 is directed to a terminal designated L, whence it proceeds to the lead 326 (see FIG. 5) and back to the integrated circuit element 322 of the phase comparator 116 for processing as described above.

Preferably, in the position indicating system 13, the parameters of the frequency-to-voltage oscillator 106, the variable resistance component 120, and the comparator 116 are adjusted or selected such that the output from the frequency-to-voltage converter 106 has a magnitude sufficient to substantially control grossly the center frequency of the output from the current controlled oscillator 102. The phase comparator 116 is adjusted to provide smaller variations in frequency necessary to correct for sensed phase differences and establish a constant phase relationship between the index signals and the frequency multiplied signals emanating from the current controlled oscillator 102. Preferably, the phase comparator 116 is adjusted such that its maximum effect on the output frequency of the voltage controlled oscillator 102 is approximately plus or minus 20% of that of the frequency-to-voltage converter 106.

Referring further to FIG. 5, there is illustrated a calibration circuit 360 for applying signals of varying frequencies to the frequency-to-voltage converter 106 and to the flip-flop 112. The purpose of this circuitry is to provide inputs of various frequencies for testing and set up of the other circuitry of the position indicating system 13, by simulating a range of frequencies which would be applied to the system 13 for various rotational speeds of the scanning unit 10. The calibration circuit includes two integrated circuit elements 362, 364 and a set of switches 366. The integrated circuit element 362, 364, upon actuation, produce signals on their various outputs having differing frequencies. The desired frequency for input to the frequency-to-voltage converter 106 and flip-flop 112 is selected by closure of the appropriate one of the switches 366.

Figure 7:
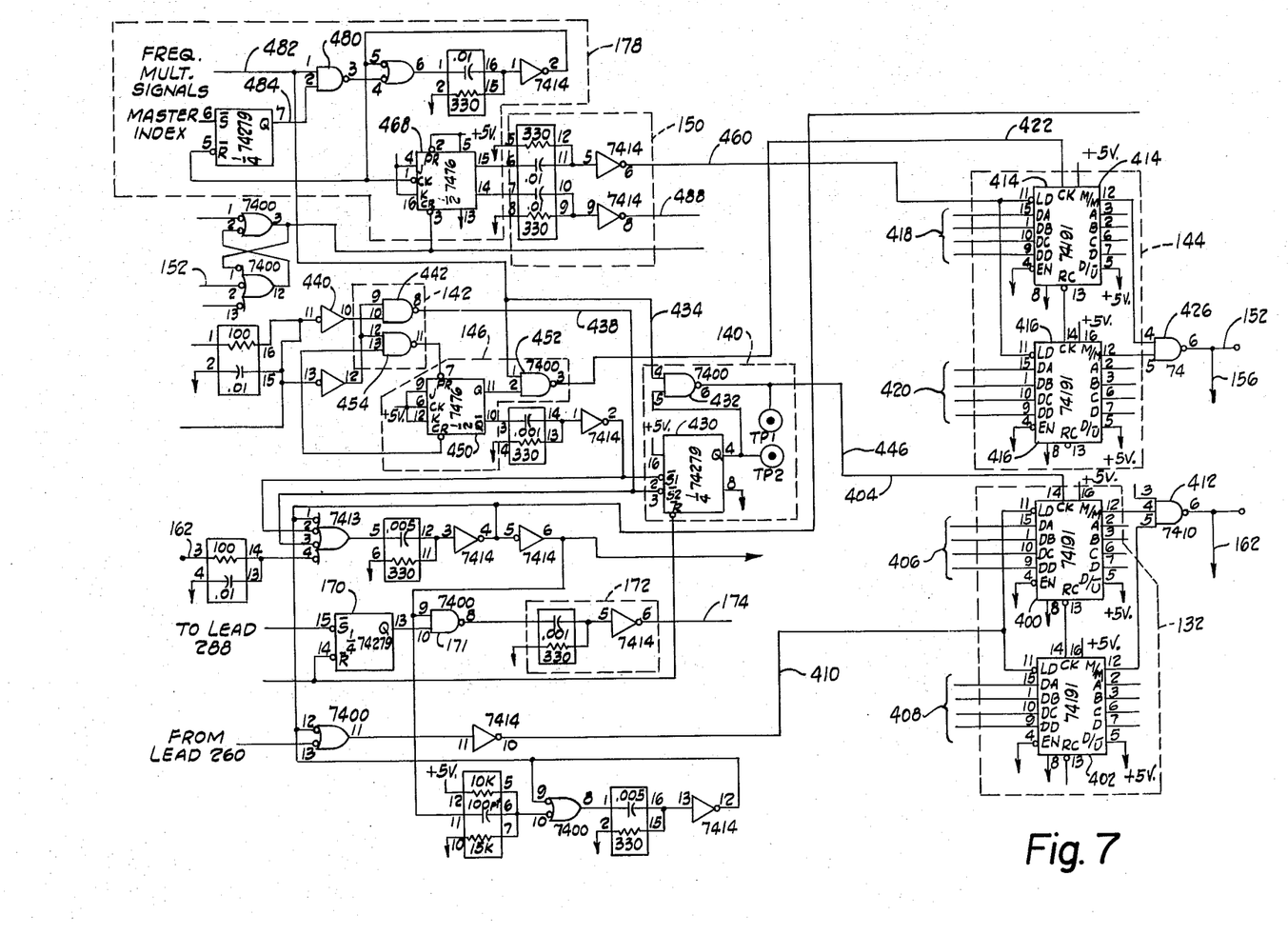

FIG. 7 shows in schematic form the portion of the processing circuitry unit 12 used for establishing the boundaries of the scanning path segments for controlling operation of the tomographic system. FIG. 7 includes the chip numbers of all integrated circuits utilized in the circuitry, and their pin number connections, along with circuit values of other elements illustrated.

The data counter 132 includes a cascaded pair of counter registers 400, 402 connected in a pattern such that the register combination counts downwardly in response to pulses applied over a lead 404. Digital binary information is applied by the computational apparatus 15 to the leads 406, 408 (represented as lead 134 in FIG. 1), for storage in the registers 400, 402, in response to a pulse signal appearing on a lead 410. This digital information represents the selected magnitude of a scan segment. A gate 412 is provided which changes its output state from high to low when the registers 400, 402 have counted down to zero from the numerical value expressed at the inputs 406, 408. This change of state in the output of the gate 412 represents the data interval signal.

The delay counter 144 includes a pair of counter registers 414, 416 coupled together in cascade in a fashion similar to that of the data counter. In a manner analogous to that of the data counter, two sets of leads 418, 420 receive digital binary signals from the computational apparatus 15 representing a predetermined magnitude of delay offset of the scan segments, when such an offset is selected. When an input is applied to the delay counter 144 by way of a lead 422, the delay counter counts down from the value established by the information present at the leads 418, 420, and when the delay counter registers 404, 406 both reach zero, they actuate a NAND gate 426 which produces a change of state on the output leads 152, 156. This change of state represents the delay interval signal.

The frequency multiplied signals are selectively applied to the lead 410 of the data counter 132 by way of the data latch 140. The data latch 140 includes an integrated circuit 430 and a NAND gate 432. The NAND gate 432 receives the frequency multiplied signals at one input over a lead 434 and has its other input connected to the integrated circuit 430. The condition of the integrated circuit 430 and the state of its output to the NAND gate 432 is controlled by the state of the signal on a lead 438 coming from the steering circuitry 142.

Referring to the left central portion of FIG. 7, the delay interval signal is applied to the steering circuitry 142 by way of the lead 152 and an inverter 440. Upon the occurrence of the delay interval signal, a steering gate 442 produces on its output lead 438 a signal which conditions the integrated circuit 430 to actuate the gate 432 to permit frequency multiplied signals appearing on the lead 434 to be applied to the data counter over a lead 446. Previous to the occurrence of the delay interval signal, the output of the gate 442 conditions the integrated circuit to prevent the passage of frequency multiplied signals to the data counter 132.

The application of the frequency multiplied signals to the delay counter is controlled by the delay latch circuit 146. The delay latch circuit 146 includes an integrated circuit 450 and a 2-input NAND gate 452. The delay latch circuit 146 is in turn controlled by the steering circuitry 142, and particularly by a NAND gate 454. When a relatively high input signal is applied to the gate 452 from the integrated circuit 450, the gate 452 allows frequency multiplied signals to pass to the delay counter by way of the lead 422. The integrated circuit 450 is controlled to provide the relatively high signal to the gate 452 during those times when the output of the gate 426, at the lead 152, has a relatively high value, by virtue of the operation of the gate 454 which receives at one of its inputs a signal from the lead 152.

It can therefore be seen that, prior to the generation of the delay interval signal, the steering circuitry 142 controls the data latch 146 to permit the application to the delay counter of frequency multiplied signals, allowing the delay counter to count down to zero, at which time the delay interval signal occurs, indicating the end of the selected delay offset as expressed by the delay magnitude signal from the computational apparatus 15.

The loading of the information at the leads 418, 420 into the delay counter 144 is initiated by the occurrence of the master index signal. When the master index signal occurs, a signal appears on a lead 460, which is applied to the loading terminals of the registers 414, 416, causing the delay counter to store the information at the terminals 418, 420.

Circuitry is also provided for initially conditioning the incoming master index and frequency multiplied signals from the incremental encoder apparatus on the scanning unit 10. This circuitry includes the synchronization circuitry 178 and the monostable multivibrator one shot circuitry 150, along with a flip-flop 468. The synchronizing circuitry includes a NAND gate 480 connected to receive frequency multiplied signals and master index signals respectively over the leads 482, 484. The NAND gate 480 provides a synchronization function in that it only produces an output upon the coincidence of a master index signal with one of the frequency multiplied signals. This feature is to assure that the system has frequency multiplied signals available immediately upon the occurrence of the master index signal.

The master index signal, after being passed through the flip-flop 468, is connected to the multivibrator, a dual one shot arrangement 150. According to the circuitry, the signal on the lead 460 undergoes an upward change of state upon the occurrence of a first master index signal, and produces an upward change of state on another lead 488 upon the occurrence of the next successive master index signal.

The signal on the lead 288 is utilized in operating termination circuitry, including the temporary memory latch 170, embodied by a flip-flop, and the one shot monostable multivibrator 172. Upon the occurrence of a second master index signal on the lead 488, the flip-flop 170 is set to apply a relatively high signal on one input of a two input NAND gate 490. The other input to the gate 490 responds to the data interval signal appearing on the lead 162. Thus, when the flip-flop 170 impresses a relatively high input on the gate 490, the gate 490 will produce a relatively low output upon the occurrence of the next to occur of the data interval signals. When the next data interval signal occurs, the output of the gate 490 changes state, and the one shot 172 produces a pulse in response on the lead 174. The lead 174 is connected to the sequencer 19, such that the operation of the entire tomographic apparatus is terminated upon the occurrence of the termination signal, represented by the pulse on the lead 174.

It is to be understood that the specific embodiment disclosed herein is illustrative, rather than exhaustive, of the invention. Persons of ordinary skill may make certain modifications, changes and additions to the embodiment as disclosed herein without departing from the spirit and scope of the invention as claimed in the appended claims.

What is claimed is:

1. A system for indicating motion of a member of a radiation sensing apparatus movable along a path, said system comprising:
   a. an incremental encoder producing index signals each indicating motion by said member past one of a plurality of locations on said path;
   b. circuitry for multiplying the frequency of said index signals by a predetermined factor to define gradations of traversal by said member between said path locations; and
   c. phase lock loop circuitry including a phase comparator having an output and being coupled to said frequency multiplying circuitry to facilitate the maintenance of a constant value for said predetermined factor so that said multiplied signals accurately represent uniform gradations of said traversal between said path locations.

2. The system of claim 1, wherein said movable member includes a radiation detector, and said radiation sensing apparatus comprises transaxial reconstruction tomographic apparatus of a type providing for rotative motion of the detector along a predetermined orbital path.

3. The system of claim 1, wherein the phase lock circuitry includes an amplifier connected between said phase comparator and said frequency multiplying circuitry, said system further comprising:
circuitry for varying the gain of the output of the phase comparator as a function of the frequency of said index signals for adjusting the gain at said phase lock loop as a function of the frequency of said index signals to maintain said loop gain at a substantially constant level to enhance the stability of said system notwithstanding changes in index signal frequency.

4. The system of claim 3 wherein:
said gain varying circuitry adjusts said gain of said phase comparator output as a substantially inverse function of said frequency of said index signals.

5. The system of claim 4, wherein said gain varying circuitry comprises:
a. an adjustable resistance component connected to said phase comparator output, and
b. a frequency to voltage connector, coupled to said encoder for controlling the resistance of said variable resistance component.

6. The system of claim 1, further comprising:
an amplifier connected between said phase comparator output and said frequency multiplier circuitry, said system further comprising:
circuitry for varying the input to said amplifier to at least grossly adjust the frequency of the output of said frequency multiplier circuitry as a function of said index signal frequency.

7. The system of claim 6 wherein said amplifier input varying circuitry comprises:
a frequency to voltage converter electrically coupled between said encoder and said amplifier.

8. A method for indicating motion of a member of a radiation sensing apparatus movable along a path, comprising the steps of:
a. producing index signals each indicating passage by said member by one of a plurality of uniformly spaced locations of said path;
b. multiplying the frequency of said index signals by a predetermined factor to define gradations of traversal by said member between said locations, and
c. producing and employing phase lock feedback signals at least partially derived from said multiplied signals to facilitate the maintenance of said factor at a constant value so that said multiplied signals accurately represent uniform gradations of said transversal between said locations.

9. The method of claim 8, wherein said feedback signal employing step is accomplished at least partially by the use of phase lock loop circuitry including a phase comparator and an amplifier connected to an output of the phase comparator, said feedback signal employing step comprising:
varying the gain of the output of the phase comparator as a function of the frequency of said index signals for adjusting the gain of said phase lock loop to maintain the gain of said loop at a substantially constant level for enhancing the stability of said loop.

10. The method of claim 8, wherein said feedback signal employing step is accomplished at least partially by the use of phase lock loop circuitry including a phase comparator connected to receive said multiplied signals and an amplifier connected to an output of the phase comparator, said feedback signal employing step comprising:
a. varying the magnitude of the input to said amplifier as a function of said index signal frequency to grossly adjust the center frequency of said multiplied signals as a function of said index signal frequency, and
b. utilizing the output from the phase comparator to finely adjust the frequency multiplier to maintain said constant phase relation.

11. A system for indicating motion of a movable information producing member of a reconstruction tomographic apparatus for examining a subject by the use of said information, including drive means for moving said member along a path, encoder apparatus for producing location signals, the occurrence of a predetermined number of such location signals indicating traversal by said movable member through a predetermined segment of said path, and processing circuitry connected to said encoder including at least partial means for operating the tomographic apparatus at least partially in response to the location signals in accordance with an operational sequence, comprising:
a. said processing circuitry including:
i. circuitry for producing a signal representing a selected magnitude of a segment of said path;
ii. data storage circuitry for storing the segment magnitude indicating signal and producing a data interval signal in response to the application thereto of a number of said location signals which correspond to traversal by said movable member over the selected segment magnitude, and
b. circuit means responsive to the data interval signal for processing said information produced by the movable member during its traversal of said path segment.

12. The system of claim 11, wherein:
said data storage circuitry comprises a data counter.

13. The system of claim 11, further comprising: circuitry for restoring in the data storage circuitry said segment magnitude signal in response to the occurrence of the data interval signal, to facilitate repetitive production of additional data interval signals by said data storage circuitry in response to the continued application of said location signals indicating traversal by said movable member of successive path segments.

14. The system of claim 11, further comprising:
a. said encoder having means for additionally producing a master index signal at a predetermined point in the motion of the movable member along said path, and
b. circuitry for initiating application of said location signals to said data storage circuitry in response to the occurrence of said master index signal.

15. The system of claim 14, wherein the processing circuitry further includes means for producing a said data interval signal indicating the traversal by said movable member of a path segment which begins at a point on said path offset by a predetermined delay interval beyond that point of said motion of said movable member at which a master index signal occurs, said means comprising:
a. circuitry for producing a signal representing a magnitude of a selected delay interval;
b. delay storage circuitry for storing the delay interval magnitude signal and being responsive to produce a delay interval signal when a number of said location signals have been applied thereto which corresponds to the motion of the movable member over the selected delay interval;

c. means responsive to the occurrence of said master index signal to load said delay interval magnitude signal into said delay storage circuitry and to substantially simultaneously initiate the application of said location signals to said delay storage circuitry, and d. circuitry responsive to the delay interval signal to initiate application of said location signals to said data storage circuitry for operating the data storage circuitry to produce said data interval signal to define a path motion segment offset from said predetermined point by said delay interval.

16. The system of claim 13, further comprising:
steering circuitry for preventing application of said location signals to said data storage circuitry while said location signals are applied to said delay storage circuitry.

17. The system of claim 16, wherein:
said steering circuitry also terminates the application of said location signals to said delay storage circuitry in response to the occurrence of said delay interval signal.

18. The system of claim 13, wherein:
a. said encoder produces a second master index signal after said master index signal, and
b. said processing circuitry further comprises termination circuitry responsive to the occurrence of said second master index signal to terminate operation of the tomographic apparatus upon the occurrence of the first data interval signal following said second master index signal.

19. The system of claim 14, wherein said processing circuitry further comprises:
circuitry connected to receive and synchronize said master index and said location signals.

20. The system of claim 11, wherein said information producing member includes a radiation detector, and said tomographic apparatus is of a type providing for rotative motion of the detector along a predetermined orbital path about the subject.

21. A method for indicating motion of a movable information producing member of a tomographic apparatus for examining a subject by the use of said information, said tomographic apparatus including drive means for moving said member along a path, encoder apparatus for producing location signals, the occurrence of a predetermined number of such location signals indicating traversal by said movable member through a predetermined segment of said path, and processing circuitry connected to said encoder forming at least partial means for operating the tomographic apparatus at least partially in response to the location signals in accordance with an operational sequence, said method comprising the steps of:

a. producing a signal representing a selected magnitude of a segment of said path;

b. storing the segment magnitude indicating signal and producing a data interval signal in response to the occurrence of a number of said location signals which correspond to traversal by said movable member over the selected segment magnitude, and c. separately processing said information produced by the movable member during its traversal of said path segment in response to the occurrence of the data interval signal.

22. The method of claim 21, further comprising the step of:
restoring said segment magnitude indicating signal in response to the occurrence of the data interval signal to facilitate repetitive production of additional data signals in response to the continued traversal of successive path segments by said movable member.

23. The method of claim 21, further comprising the steps of:
a. producing a master index signal at a predetermined point in the motion of said movable member along said path;
b. producing a said data interval signal indicating the traversal by said movable member of a path segment which begins at a point on said path offset by a predetermined delay interval from that point of said motion at which said master index signal occurs, comprising the steps of:
    i. producing a signal representing a magnitude of a selected delay interval along said path;
    ii. storing the delay interval magnitude signal and producing a delay interval signal in response to the occurrence of a number of location signals corresponding to motion of the movable member over said delay interval of said path;
    iii. producing a said data interval signal in response to the occurrence of the delay interval signal to define a path motion segment offset from said predetermined point by said delay interval.

24. The method of claim 21, further comprising the steps of:
a. producing a termination signal, and
terminating operation of the tomographic apparatus in response to the occurrence of a first data interval signal following said termination signal.

25. A reconstruction transaxial tomographic apparatus for sensing radiation from a subject and for developing portions of information from such sensed radiation and producing an image therefrom indicating a condition of the subject, said apparatus comprising:
a. a radiation detector mounted for motion about the subject along an orbital path;
b. power means for moving the detector along the path;
c. an incremental encoder for producing index signals each indicating motion of said detector past one of a plurality of uniformly spaced predetermined locations on said path;
d. circuitry for multiplying the frequency of said index signals by a predetermined factor to indicate gradations of said motion between two of said locations;
e. phase lock loop circuitry including a phase comparator connected to the frequency multiplying circuitry to facilitate the maintenance of a uniform frequency multiplication ratio between the multiplied and index signals so that the multiplied signals accurately represent uniform increments of said motion between said path locations; and
f. means connected to the frequency multiplier circuitry and said detector for developing information about a condition of the subject at least partly in response to said sensed radiation with the motion indicating multiplied signals, and for operating the tomographic apparatus at least partially in response to the multiplied signals.

26. The system of claim 25, wherein the information developing means comprises:
   a. means for producing a signal representing a selected magnitude of detector motion along a segment of said path;
   b. a data counter for storing the segment magnitude indicating signal and being responsive to said multiplied signals to produce a data interval signal when a number of multiplied signals has occurred which corresponds to motion of the detector over the selected path segment magnitude, and
   c. means responsive to the data interval signal for separately processing radiation sensing information produced by the detector during its motion through said segment.

27. The system of claim 25, further comprising:
   means for restoring in the data counter the segment magnitude indicating signal in response to the occurrence of the data interval signal, to facilitate repetitive operation of the data counter to produce additional data interval signals as the detector traverses additional segments of motion along said orbital path.

28. The system of claim 25, wherein:
   a. said incremental encoder comprises means for producing a master index signal substantially coincidental with an index signal at a predetermined point in the motion of the detector, and
   b. said data counter commences to respond to the index signals coincidentally with the occurrence of said master index signal.

29. The system of claim 28, wherein the information developing means further includes additional circuitry for producing a said data interval signal indicating motion of the detector through a motion segment beginning at a point on said path displaced by a delay interval from the predetermined point of the detector motion indicated by the occurrence of said master index signal, said additional circuitry comprising:
   a. means for producing a signal representing a magnitude of a selected delay interval;
   b. a delay counter for storing the delay magnitude signal and being responsive to the application thereto of said frequency multiplied signals to produce a delay interval signal when a number of said multiplied signals have been so applied which correspond to detector motion over the selected delay interval;
   c. means responsive to the occurrence of said master index signal to load said delay magnitude signal into said delay storage counter and to initiate the application of said multiplied signals to said delay storage counter, and
   d. circuitry responsive to said delay interval signal to initiate application of said frequency multiplied signals to the data counter to facilitate the delineation of the delayed motion.

30. The system of claim 29, further comprising:
   steering circuitry for preventing application of said multiplied signals to said data counter while said multiplied signals are applied to said delay counter.

31. The system of claim 29, further comprising:
   steering circuitry responsive to said delay interval signal for initiating the application of said multiplied signals to said data counter.

32. The system of claim 31, wherein:
   said steering circuitry also terminates the application of said multiplied signals to said delay counter in response to the occurrence of said delay interval signal.

33. The system of claim 27, wherein:
   a. said incremental encoder produces a second master index signal after said master index signal;
   b. said information developing circuitry further comprises termination circuitry responsive to the occurrence of said second master index signal to terminate operation of the tomographic apparatus upon the next occurring data interval signal from said data counter.

34. The system of claim 28, further comprising:
   circuitry connected to receive and synchronize said master index and said multiplied signals prior to their input to said processing circuitry.

35. The system of claim 25, wherein said tomographic apparatus is of a radiographic type having a radiation source also mounted for orbital motion synchronously with the detector about the subject for directing X-rays through the subject toward the detector.

36. A system for indicating the position of a movable radiation detector in a tomographic apparatus for producing an image representing radiation from a subject, the apparatus including drive structure for moving the detector along a predetermined path with uniform speed and circuitry connected to the detector for processing output signals from the radiation detector generated during detector movement over a succession of segments of said path, said system comprising:
   a. apparatus for producing an index signal whenever said radiation detector passes between an adjacent pair of said path segments, and
   b. electrical means for multiplying the frequency of occurrence of said index signals by a predetermined factor to provide a plurality of multiplied electrical signals occurring between each adjacent pair of said index signals, said frequency multiplied signals being usable when applied to said processing circuitry to indicate by interpolation the position of the detector when traveling at uniform speed between the boundaries of one of said path segments.

37. The system of claim 36, wherein said frequency multiplication circuitry comprises:
   phase lock loop feedback circuitry for maintaining a uniform frequency multiplication ratio between the index and frequency and multiplied signals, so that the frequency multiplied signals accurately indicate the position of the detector when traveling between the boundaries of one of said path segments.

38. Processing control circuitry for a radiation sensing apparatus having a member for producing information in response to radiation from a subject and being movable along a path, drive structure for moving the member, and means responsive to discrete portions of said information produced during traversal by said member of segments of said path to produce an image of a portion of the subject, said processing control circuitry comprising:
   a. circuitry for adjustably defining the magnitude of a path segment;
   b. circuitry for sensing the motion of the movable member; and
   c. circuitry for producing an indication to said image producing means defining when the movable member crosses a boundary of said path segment.

39. The circuitry of claim 38, further comprising:
offset circuitry connected to and causing the indication producing circuitry to indicate traversal by said member across the boundaries of a path segment of said predetermined magnitude having a boundary offset by a predetermined distance from a predetermined point on said path.

40. The circuitry of claim 39, wherein said predetermined distance is adjustable.

41. The circuitry of claim 38, further comprising: termination circuitry for stopping an operation of the radiation sensing apparatus in response to the passage of the movable member past a predetermined location on said path.

42. A system for indicating motion of a movable member of a radiation sensing apparatus movable along a path, comprising:
 a. means for producing index signals each indicating passage of the member past a predetermined location on the path, and
 b. means for multiplying the index signals to indicate gradations of said motion intermediate said predetermined locations.

43. The system of claim 42, further comprising: feedback control circuitry for maintaining a substantially constant frequency multiplication ratio between the index and multiplied signals.

44. The system of claim 42 further comprising: means for adjusting a parameter of said feedback circuitry in response to the frequency of said index signal.

45. A system for indicating motion of a member of radiation sensing apparatus movable along a path, said system comprising:
 a. encoder means responsive to movement of the member for producing index signals representative of a motion by said member past a plurality of locations on said path;
 b. circuit means responsive to an error compensating signal for conditioning said index signals by a predetermined factor to generate conditioned index signals representative of gradations of traversal by said member between said path locations; and,
 c. compensating circuitry responsive to said conditioned index signals and to said index signals for generating the error compensating signal to thereby facilitate the maintenance of a constant value for said predetermined factor so that said conditioned index signals accurately represent uniform gradations of said traversal between said path locations.

46. A method for indicating motion of a member of a radiation sensing apparatus movable along a path, comprising the steps of:
 a. producing index signals indicating traversal by said member past a plurality of locations uniformly spaced along said path;
 b. conditioning said index signals by a predetermined factor to generate conditioned index signals which define gradations of traversal by said member between said locations, and
 c. producing and employing feedback compensating signals at least partially derived from said conditioned index signals to facilitate the maintenance of said factor at a constant value so that said conditioned index signals accurately represent uniform gradations of said traversal between said locations.

47. A system for indicating motion of a movable information producing member of a tomographic apparatus which reconstructs an image of a section of a subject by the use of said information, including drive means for moving said member along a path, encoder apparatus for producing location signals indicating traversal by said movable member through a series of segments comprising said path, and processing circuitry connected to said encoder apparatus for operating on the information to produce said image in response to the location signals, comprising:
 a. said processing circuitry including:
  i. circuitry for producing a signal indicative of a preselected magnitude of several segments of said path;
  ii. data storage circuitry for storing the segment magnitude indicating signal and producing in response to said location signals data interval signals corresponding to traversal by said movable member through the segments having the selected segment magnitudes, and
 b. circuit means responsive to the data interval signals for separately processing the information produced by the movable member during its traversal of each path segment.

48. A method for indicating motion of a movable information producing member of a tomographic apparatus which reconstructs an image of a section of a subject by the use of said information, said tomographic apparatus including drive means for moving said member along a path, encoder apparatus for producing location signals indicating traversal by said movable member through a series of segments constituting said path, and processing circuitry connected to said encoder apparatus for operating on the information to produce said image in response to the location signals, said method comprising the steps of:
 a. producing a signal representing a selected magnitude of several segments of said path;
 b. producing data interval signals in response to the location signals corresponding to traversal by said movable member over path segments of the selected segment magnitude; and,
 c. separately processing the information produced by the movable member during its traversal of each path segment in response to the occurrence of the data interval signals.

49. A system for indicating the position of a movable radiation detector in a tomographic apparatus which produces an image representing radiation emanating from a subject, the apparatus including drive structure for moving the detector along a predetermined path with substantially uniform speed and circuitry connected to the detector for processing output signals generated by the radiation detector during detector movement over a succession of adjoining segments constituting said path, said position indicating system comprising:
 a. apparatus coupled to the radiation detector for producing an index signal indicative of the radiation detector passing a boundary of adjacent path segments; and,
 b. electrical means for conditioning said index signals by a predetermined factor to provide conditioned index signals indicative of interpolation of the position of the detector as it travels between the boundaries of the respective path segments, wherein said conditioned index signals are soupled to said processing circuitry for precisely defining the boundaries of said segments.

50. Processing control circuitry for a radiation sensing apparatus having a member for producing radiation intensity information in response to radiation from a subject, drive structure for moving the member along a path, and image producing means responsive to discrete portions of said information respectively produced during traversal by said member of path segments of known magnitude constituting said path for producing an image of a section of the subject, said processing control circuitry comprising:

a. circuitry for adjustably defining the boundaries of respective path segments in response to a prespecified signal;

b. means responsive to the motion of the movable member through the respective path segments for producing indications to said image producing means defining when the movable member crosses said boundaries of the respective path segments; and c. means coupled to the defining circuitry for generating the prespecified signal.

* * * * *